United States Patent
Zink et al.

(10) Patent No.: US 11,786,181 B2
(45) Date of Patent: Oct. 17, 2023

(54) MAGNETIC RESONANCE APPARATUS WITH A PATIENT POSITIONING APPARATUS

(71) Applicant: Siemens Healthcare GmbH, Erlangen (DE)

(72) Inventors: Stephan Zink, Bayern (DE); Rainer Kurth, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/554,228

(22) Filed: Dec. 17, 2021

(65) Prior Publication Data

US 2022/0192603 A1 Jun. 23, 2022

(30) Foreign Application Priority Data

Dec. 18, 2020 (EP) .................................... 20215732

(51) Int. Cl.
*A61B 5/00* (2006.01)
*A61B 5/055* (2006.01)

(52) U.S. Cl.
CPC .............. *A61B 5/704* (2013.01); *A61B 5/055* (2013.01)

(58) Field of Classification Search
CPC ........ A61B 5/704; A61B 5/055; A61G 13/00; A61G 13/06; A61G 13/04; A61G 13/08; G01R 33/3664; G01R 33/56375; G01R 33/56383
See application file for complete search history.

(56) References Cited

U.S. PATENT DOCUMENTS

| | | | |
|---|---|---|---|
| 7,034,535 B2 * | 4/2006 | Yamagata | A61B 5/055 324/309 |
| 2003/0062898 A1 * | 4/2003 | Imai | A61B 5/055 324/318 |
| 2007/0143921 A1 * | 6/2007 | Hiyama | A61B 5/055 5/601 |
| 2013/0008726 A1 | 1/2013 | Eberler et al. | |
| 2013/0235969 A1 * | 9/2013 | Winter | A61N 5/1079 378/4 |
| 2020/0054240 A1 * | 2/2020 | Roland | G01R 33/543 |

FOREIGN PATENT DOCUMENTS

| | | |
|---|---|---|
| CN | 210301002 U | 4/2020 |
| DE | 102011078567 A1 | 1/2013 |
| DE | 102018213781 A1 | 2/2020 |

* cited by examiner

*Primary Examiner* — Boniface Ngathi
*Assistant Examiner* — Milton Truong
(74) *Attorney, Agent, or Firm* — Banner & Witcoff Ltd.

(57) ABSTRACT

The present disclosure relates to a magnetic resonance apparatus having a scanner unit, a patient receiving region at least partially surrounded by the scanner unit, and a patient positioning apparatus, which has a patient table that is movable within the patient receiving region. The patient positioning apparatus may include a vertical adjusting unit for an adjustment of a vertical position of the patient table within the patient receiving region, and the vertical adjusting unit nay include at least two different vertical positions for a positioning of the patient table within the patient receiving region.

17 Claims, 3 Drawing Sheets

MAGNETIC RESONANCE APPARATUS WITH A PATIENT POSITIONING APPARATUS

CROSS-REFERENCE TO RELATED APPLICATIONS

Figure 1:
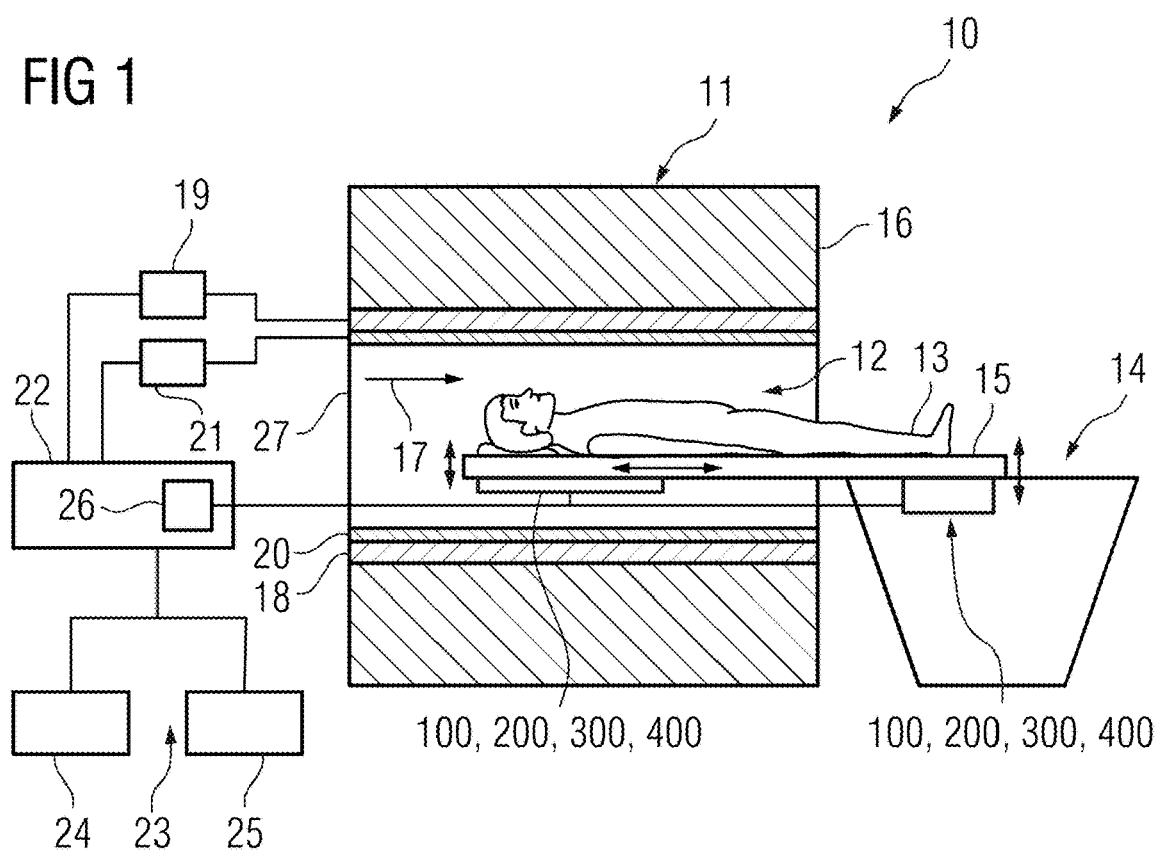

The present application claims the benefit of the filing date of European patent application no. EP 20215732.7, filed on Dec. 18, 2020, the contents of which are incorporated herein by reference in their entirety.

TECHNICAL FIELD

The present disclosure relates to a magnetic resonance apparatus having a scanner unit, a patient receiving region at least partially surrounded by the scanner unit, and a patient positioning apparatus, which has a patient table that is movable within the patient receiving region.

BACKGROUND

Magnetic resonance apparatuses typically have a patient receiving region in which a patient is supported and/or positioned for an examination, e.g. a magnetic resonance examination. Preferably, the patient, in particular, the region of the patient to be examined, is to be positioned in an isocenter of the magnetic resonance apparatus in order to obtain ideal conditions for a capture of magnetic resonance data. For this purpose, the patient is positioned on a patient table of a patient positioning apparatus. Particularly in the case of cylindrically formed patient receiving regions of magnetic resonance apparatuses, the patient table has a single position in the vertical direction within the patient receiving region. For an average patient, this position enables a substantially optimum positioning within the patient receiving region, in particular, with regard to the isocenter of the magnetic resonance apparatus. However, this position represents a compromise in the positioning in the vertical direction for patients who, due to their anatomy, diverge greatly from an average patient. The position of the patient table is also not configured to be adjustable and/or settable in the vertical direction. This leads to, independently of a patient anatomy and/or a type of the magnetic resonance examination, the patient table always assuming the same position in the vertical direction.

Where there is a greater space requirement in the vertical direction, the spine radiofrequency coil arranged on and/or in the patient table can be removed from the patient table for the current examination of the patient. However, this radiofrequency coil may then no longer be available for a data capture, so that thereby the image data quality can be negatively influenced. For small patients, for example children, it is known that positioning cushions can be used for optimal positioning in order to arrange and/or position a region of the patient to be examined in the isocenter of the magnetic resonance apparatus. However, during an examination of the spinal column, this can lead to a significant weakening of the signal and thus to an impairment of an image quality in the magnetic resonance image data captured.

SUMMARY

It is an object of the present disclosure to make a position of the patient table adjustable in the vertical direction within a patient receiving region. The object is achieved in accordance with the embodiments as described herein, including the features of the claims.

The present disclosure relates to a magnetic resonance apparatus having a scanner unit, a patient receiving region at least partially surrounded by the scanner unit, and a patient positioning apparatus, which has a patient table that is movable within the patient receiving region. According to the disclosure, the magnetic resonance apparatus has a vertical adjusting unit for an adjustment of a vertical position of the patient table within the patient receiving region, wherein the vertical adjusting unit comprises at least two different vertical positions for a positioning of the patient table within the patient receiving region.

The magnetic resonance apparatus may comprise a medical and/or diagnostic magnetic resonance apparatus, which is designed and/or configured for capturing medical and/or diagnostic image data, e.g. medical and/or diagnostic magnetic resonance image data of a patient. For this purpose, the magnetic resonance apparatus comprises the scanner unit. The scanner unit of the magnetic resonance apparatus e.g. comprises a detector unit, such as a magnet unit for capturing the medical and/or diagnostic image data. The scanner unit herein comprises, e.g., the magnet unit, a main field magnet, a gradient system, and a radiofrequency antenna unit. The radiofrequency antenna unit is arranged within the scanner unit in a fixed manner and is designed and/or configured for emitting an excitation pulse. In addition, the magnetic resonance apparatus has at least one local radiofrequency coil, which is configured for receiving a magnetic resonance signal. For this purpose, the local radiofrequency coil is arranged and/or placed round the region of the patient that is to be investigated. The individual local radiofrequency coils are specifically designed and/or configured for an examination region of patients, for example, a radiofrequency head coil or a radiofrequency knee coil, etc.

The main field magnet is configured for generating a homogeneous main magnetic field with a defined magnetic field strength, for example, a magnetic field strength of 3 T or 1.5 T, etc. The main field magnet is configured for generating a strong and constant main magnetic field. The homogeneous main magnetic field may be arranged and/or to be found within a patient receiving region of the magnetic resonance apparatus. The gradient system is configured for generating magnetic field gradients that are used for position encoding during an imaging process.

The patient receiving region is designed and/or configured for receiving the patient, e.g., the region of the patient to be investigated, for a medical magnetic resonance examination. For example, for this purpose the patient receiving region is configured as cylindrical and/or is cylindrically surrounded by the scanner unit, e.g. the magnet unit of the magnetic resonance apparatus. A field of view (FOV) and/or an isocenter of the magnetic resonance apparatus may be arranged within the patient receiving region. The FOV may comprise a capture region of the magnetic resonance apparatus, within which the conditions exist for a capture of medical image data, e.g. magnetic resonance image data, within the patient receiving region, for example, a homogeneous main magnetic field. The isocenter of the magnetic resonance apparatus may comprise the region and/or point within the magnetic resonance apparatus that has the optimal and/or ideal conditions for the capture of medical image data. For example, the isocenter may comprise the most homogeneous magnetic field region within the magnetic resonance apparatus.

For a positioning of the patient, e.g. the region of the patient to be investigated, within the patient receiving region, the magnetic resonance apparatus has the patient positioning apparatus. The patient positioning apparatus is configured for a positioning of the patient. The patient positioning apparatus may have a movable patient table which is configured to be movable, e.g., within the patient receiving region of the magnetic resonance apparatus. For a magnetic resonance examination, the patient is firstly positioned on the patient table of the patient positioning apparatus and subsequently the patient table is moved together with the patient into the patient receiving region, until the region of the patient to be investigated is positioned within the isocenter.

The vertical adjusting unit of the magnetic resonance apparatus is configured to set a vertical position of the patient table. The vertical adjusting unit may have a vertical adjusting element or a plurality of vertical adjusting elements, which can be arranged on the patient positioning apparatus, for example, on the patient table and/or within the patient receiving region. The vertical adjusting unit, e.g. the individual vertical adjusting elements of the vertical adjusting unit, may be configured to make available at least two different vertical positions for the positioning of the patient table in the vertical direction and/or to adjust a position of the patient table in the vertical direction in one of the at least two different vertical positions. The vertical adjusting unit, e.g. the individual vertical adjusting elements of the vertical adjusting unit, may be configured so that the adjustment can take place between the at least two different vertical positions via different position steps, e.g. defined and/or fixed position steps. Alternatively, for this purpose the vertical adjusting unit may also comprise an adjusting region, e.g. a vertical adjusting region, wherein the at least two different vertical positions are adjustable as desired, e.g. freely selectable by a user, within the adjusting region.

The vertical adjusting unit may have at least three different vertical positions for a positioning of the patient table in the vertical direction within the patient receiving region. For example, a middle vertical position of the three vertical positions may comprise a base position of the patient table in the vertical direction, wherein the middle vertical position and/or the base position of the patient table in the vertical direction may be used e.g. for patients with an average anatomy. A lower vertical position of the three vertical positions may be used, e.g. for patients with a larger than average anatomy, for example, for relatively adipose patients and/or for patients with a greater space requirement, since then more usable space exists between the patient table, e.g. a positioning region of the patient table for positioning the patient, and a housing surrounding the patient receiving region. An upper vertical position of the three vertical positions can be used, e.g. for patients with a smaller than average anatomy, for example, for children, to position the region of the patient to be investigated within the isocenter of the magnetic resonance apparatus.

For an adjustment of a vertical position of the patient table from a plurality of available vertical positions, the patient receiving region has any suitable diameter and/or a transverse extent of greater than 50 cm. For example, the patient receiving region may be a diameter and/or a transverse extent of greater than 60 cm, of greater than 70 cm, of greater than 75 cm, of greater than 80 cm, etc.

The embodiments of the disclosure have the advantage that a positioning of the patient table is possible in the vertical direction within the patient receiving region. For instance, the positioning of the patient table in the vertical direction can herein be adapted to an anatomy of the patient and/or to a type of the magnetic resonance examination. For instance, in a magnetic resonance examination with a greater space requirement within the patient receiving region, the patient table can be placed and/or driven into a lower vertical position and thus more space can be made available for the patient and/or for additional units on the patient table. Magnetic resonance examinations with a greater space requirement can comprise, for example, magnetic resonance examinations of corpulent patients and/or magnetic resonance examinations in which a greater space requirement is created by the placement of additional units on the patient table, for example, examinations of a breast and/or a knee and/or a prostate gland of patients. Therein, in the case of patients who are overweight and/or suffer from claustrophobia, more space can be provided during a magnetic resonance examination.

A further advantage of the disclosure is that the region of a patient that is to be examined can be arranged in a targeted manner in the vertical direction within the isocenter for the magnetic resonance examination to be carried out. In addition, in examinations on children and/or very thin patients for whom the region to be investigated would be below the isocenter in a normal position of the patient table, the patient table can also be placed and/or driven into a higher vertical position in order thereby to position the region of the patient to be examined within the isocenter of the magnetic resonance apparatus.

In an advantageous development of the magnetic resonance apparatus according to the disclosure, it can be provided that the vertical adjusting unit comprises at least one vertical adjusting element which is arranged within the patient receiving region. Therein, the at least one vertical adjusting element can comprise a vertical adjusting element, which is configured for receiving the patient table in a vertical position, for example, a defined vertical position. In addition, the at least one vertical adjusting element may also comprise an active vertical adjusting element, which is configured for direct adjustment of a defined vertical position of the patient table. An arrangement within the patient receiving region of the at least one vertical adjusting element should be understood herein to be, e.g. an arrangement of the at least one vertical adjusting element on a housing surrounding the patient receiving region. By means of the arrangement of at least one vertical adjusting element of the vertical adjusting unit within the patient receiving region, a particularly compact arrangement of the vertical adjusting unit can be achieved.

In an advantageous development of the magnetic resonance apparatus according to the disclosure, it can be provided that the at least one vertical adjusting element comprises a side guide for the patient table with two different receiving regions for receiving the patient table. The side guide for the patient table may be arranged within the patient receiving region and is configured for guiding the patient table within the patient receiving region. The side guide herein extends on an edge region of the patient receiving region. The two side guides can therein be integrated into a housing of the patient receiving region. Two side guides may be arranged within the patient receiving region for guiding the patient table within the patient receiving region, wherein the two side guides are arranged at different, e.g. mutually opposing, sides of the patient receiving region. The patient table of the patient positioning apparatus is guided between the two side guides within the patient receiving region.

Each of the two side guides may have at least two different receiving regions for receiving the patient table and thus also have at least two different vertical positions for the positioning of the patient table, so that at least two different vertical positions are available for the patient table. Each of the two side guides may have three different receiving regions for receiving the patient table, so that three different vertical positions are available for the patient table for adjusting a vertical position of the patient table. The individual receiving regions may be configured as guide rails for guiding and/or receiving the patient table. For instance, the different receiving regions may differ with regard to their arrangement in the vertical direction on the side guides.

One advantage of such a configuration is that a vertical adjusting unit that is simple in design, is particularly economical, and may be provided for setting a position of the patient table.

In an advantageous development of the magnetic resonance apparatus according to the disclosure, it can be provided that the vertical adjusting unit comprises at least one vertical adjusting element, which is arranged on a rear-side opening of the patient receiving region for receiving the patient table. For instance, the vertical adjusting element may be configured for supporting a patient table that is mounted at least partially floatingly within the patient receiving region. Herein, the at least partially floatingly mounted patient table protrudes with an end at the front in the introducing direction into the patient receiving region, and is mounted only with a rear end on the patient positioning apparatus. The vertical adjusting element may be adjusted and/or set before a reception and/or support of the end of the patient table, which freely protrudes into the patient receiving region to a height and/or a vertical position of the patient table. For the support of the patient table, the vertical adjusting element may also protrude from the rear-side opening into the patient receiving region, so that the patient table may already be received by the vertical adjusting element starting from, for example, a center of the patient receiving region. With this embodiment of the disclosure, an undesirable sagging of the patient table can be prevented.

In an advantageous development of the magnetic resonance apparatus according to the disclosure, it can be provided that the at least one vertical adjusting element has an active vertical adjusting element for a direct adjustment of a vertical position of the patient table within the patient receiving region. For example, such an active vertical adjusting element may be configured for adjusting and/or adapting at least one guide element, for example, a guide rail for guiding the patient table in a vertical direction within the patient receiving region. A vertical adaptation of the at least one guide element may take place dependent upon a vertical position and/or a height of the patient table. The active vertical adjusting element may comprise, for example, a scissor lift and/or further active vertical adjusting elements that a person skilled in the art deems useful. By this means, a simple and direct adjustment of a vertical position of the patient table can be achieved.

In an advantageous development of the magnetic resonance apparatus according to the disclosure, it may be provided that the vertical adjusting unit has at least one vertical adjusting element which is arranged on the patient positioning apparatus. The at least one vertical adjusting element on the patient positioning apparatus may comprise an active vertical adjusting element, which is configured for direct adjustment of a vertical position of the patient table. The at least one active vertical adjusting element may therein be configured for adjusting a vertical position of the patient table if the patient table is still situated in a starting position. In the starting position of the patient table, it is still completely outside the patient receiving region. In addition, the at least one active vertical adjusting element may also be configured for adjusting a vertical position of the patient table if the patient table is already situated in an in-bore position. In the in-bore position of the patient table, the patient table is situated at least partially within the patient receiving region. This embodiment of the disclosure has the advantage that no additional structural space is needed within the patient receiving region for adjusting a vertical position of the patient table, and thus an advantageous space provision is made available for the patient during a magnetic resonance measurement.

In an advantageous development of the magnetic resonance apparatus according to the disclosure, it can be provided that the at least one vertical adjusting element is arranged on an underside of the patient table. The underside of the patient table comprises a side and/or surface of the patient table facing away from a positioning region for the patient. This embodiment enables a particularly space-saving arrangement of the patient table. In addition, in this way a high degree of safety can be achieved for the patient, since an injury caused by the at least one vertical adjusting element can advantageously be prevented due to the arrangement of the at least one vertical adjusting element on the underside of the patient table. The at least one vertical adjusting element can thereby comprise an active vertical adjusting element, for example, at least one scissor lift arranged on the underside of the patient table and/or further active vertical adjusting elements that a person skilled in the art deems useful.

In an advantageous development of the magnetic resonance apparatus according to the disclosure, it can be provided that the vertical adjusting unit has at least one vertical adjusting element, wherein the at least one vertical adjusting element comprises a scissor lift. By this means, a particularly economical vertical adjusting unit for adjusting a vertical position of the patient table can be provided. For instance, in this way the individual vertical positions of the patient table may also be adjusted with any desired heights and/or positions in the vertical direction within an adjusting region and are thereby not restricted to pre-determined and/or fixed positions.

In an advantageous development of the magnetic resonance apparatus according to the disclosure, it may be provided that the vertical adjusting unit comprises a vertical adjusting region and the at least two vertical positions are adjustable as desired within the vertical adjusting region. For instance, the vertical adjusting region comprises, for the at least two vertical positions, a minimum vertical position and a maximum vertical position, wherein the at least two adjustable vertical positions of the patient table can be adjusted as desired between the minimum vertical position and the maximum vertical position. In this way, a particularly flexible and/or dynamic adjustment of a vertical position may be achieved for the patient table.

In an advantageous development of the magnetic resonance apparatus according to the disclosure, it may be provided that the patient positioning apparatus comprises a patient table control unit, which is configured for controlling the vertical adjusting unit, e.g. the individual vertical adjusting elements of the vertical adjusting unit. Thus, the patient table control unit may also be configured for the control of a position adjustment, e.g. an adjustment of a vertical position, of the patient table.

The patient table control unit comprises at least one computation module and/or a processor. For instance, the patient table control unit may be configured to carry out computer-readable instructions which are stored in a storage unit of the patient table control unit. The components of the patient table control unit may be configured mainly in the form of software components. In principle, these components can also be realized partially, e.g. if particularly rapid calculations are involved, in the form of software-supported hardware components, for example, FPGAs or the like. Similarly, the required interfaces may be configured, for example, where only an acceptance of data from other software components is concerned, as software interfaces. However, these may also be configured as interfaces which are constructed as hardware and are controlled by suitable software. It is also conceivable that a plurality of the aforementioned components are realized in the form of an individual software component and/or a software-supported hardware component.

By means of the patient table control unit, an advantageous adjustment of the individual vertical adjusting elements may take place for adjusting a vertical position of the patient table. For instance, in this way vertical adjusting elements on the patient positioning apparatus and the vertical adjusting elements can advantageously be matched to one another within the patient receiving region for an adjustment of a vertical position of the patient table.

BRIEF DESCRIPTION OF THE DRAWINGS/FIGURES

Further advantages, features and details of the disclosure are disclosed in the following description of exemplary embodiments and the drawings.

Figure 2:
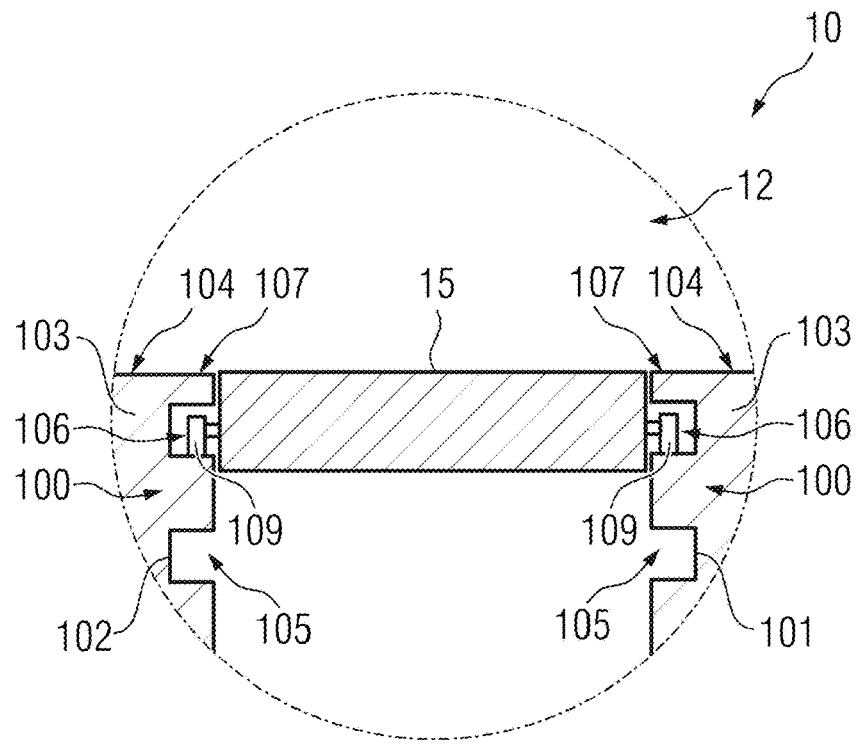
Figure 3:
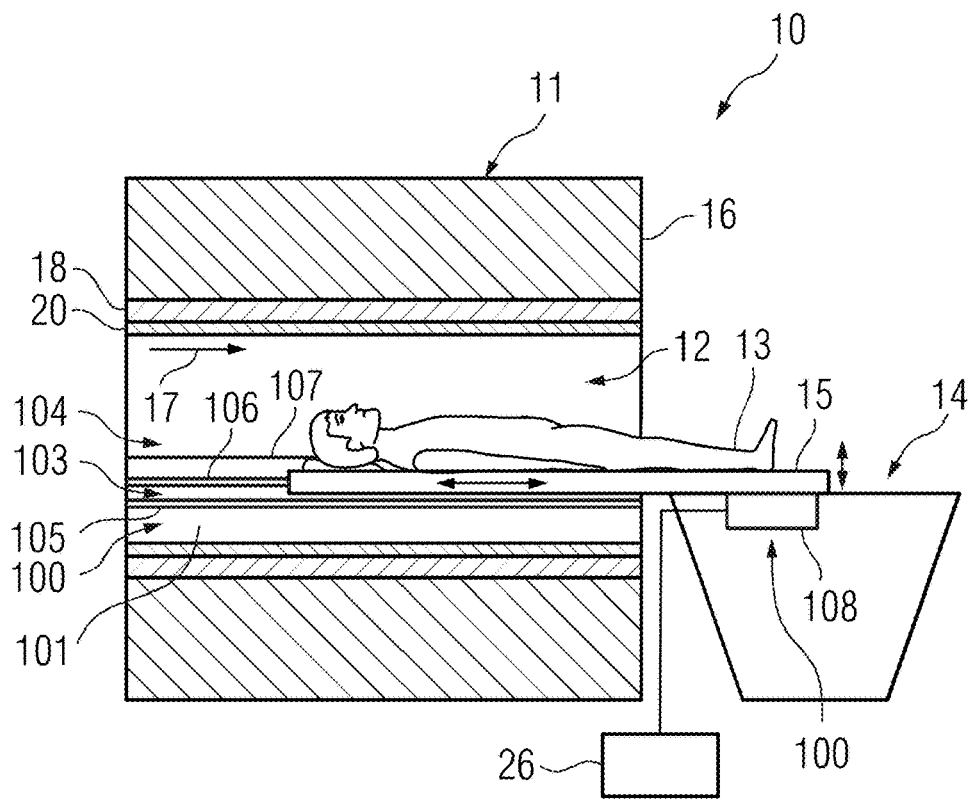
Figure 4:
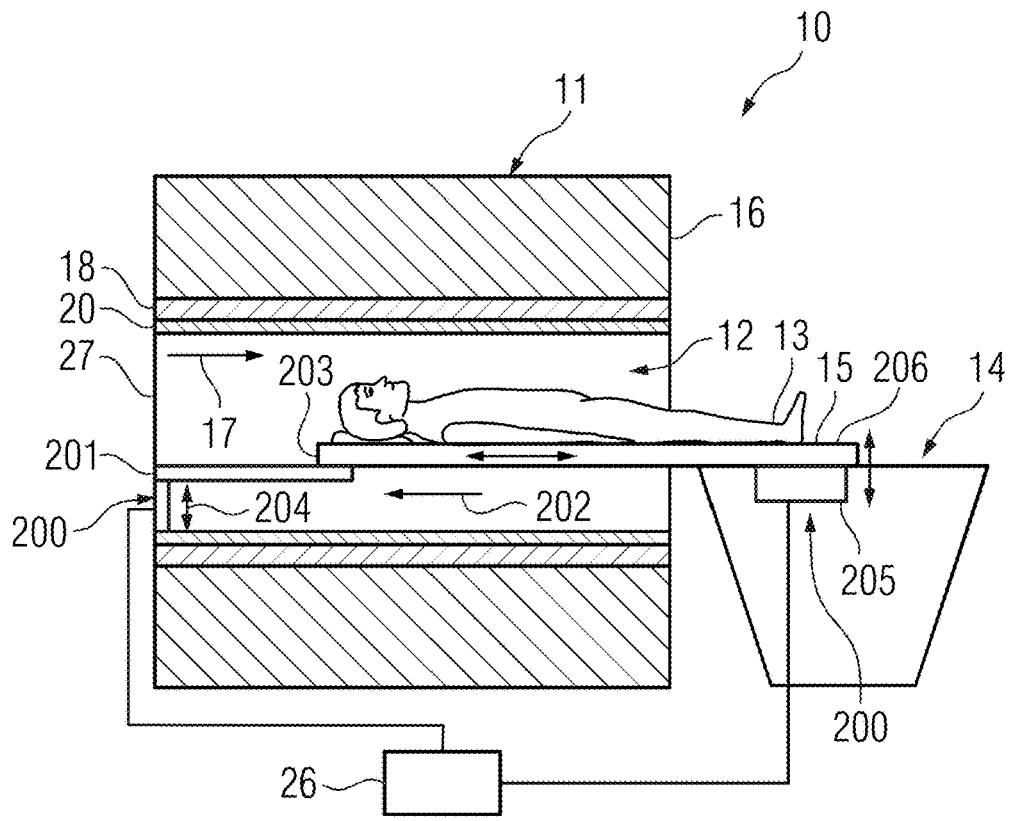
Figure 5:
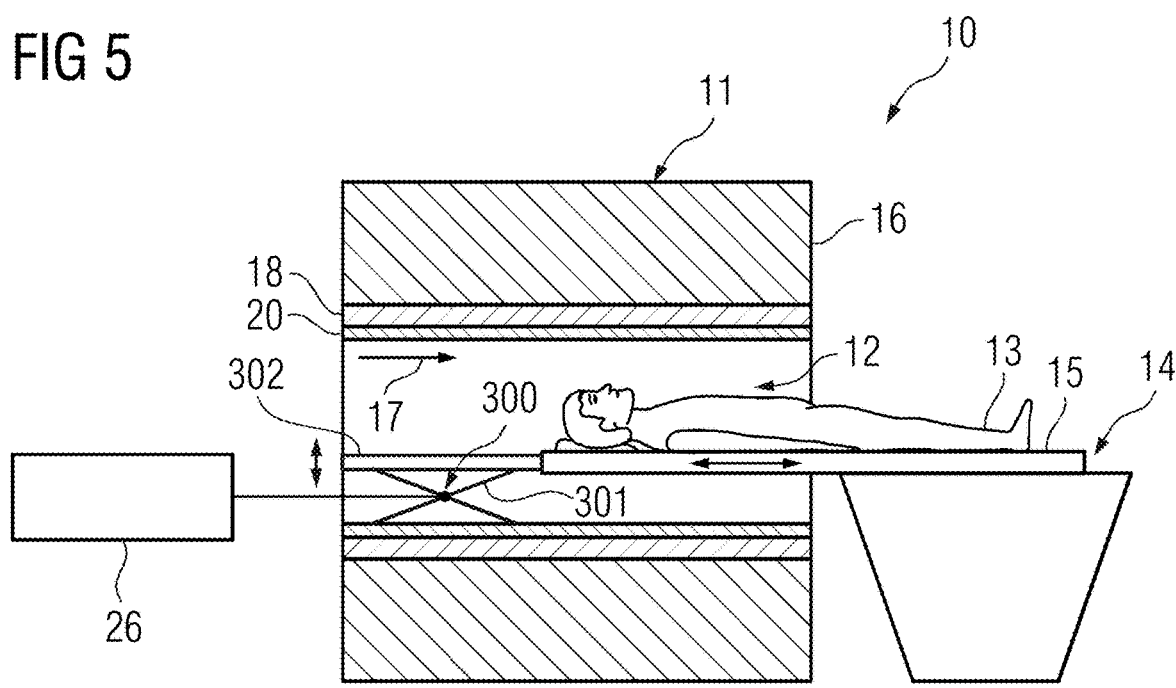
Figure 6:
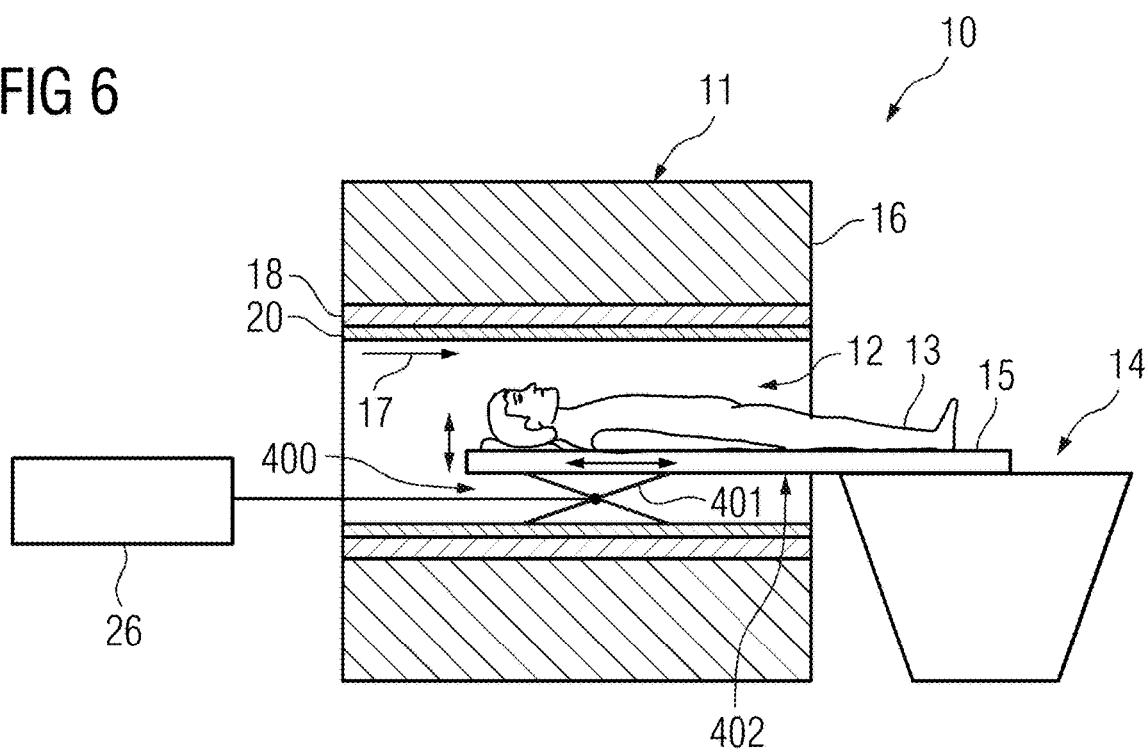

In the drawings:

FIG. 1 shows a schematic representation of an example magnetic resonance apparatus according to the one or more embodiments of the disclosure with a patient positioning apparatus, FIG. 2 shows a first exemplary embodiment of an example vertical adjusting unit with at least one vertical adjusting element within a patient receiving region of the magnetic resonance apparatus, FIG. 3 shows the magnetic resonance apparatus with the first exemplary embodiment of the vertical adjusting unit in a side view, FIG. 4 shows a second exemplary embodiment of a vertical adjusting unit with at least one vertical adjusting element within a patient receiving region of the magnetic resonance apparatus, FIG. 5 shows a third exemplary embodiment of a vertical adjusting unit with at least one vertical adjusting element within a patient receiving region of the magnetic resonance apparatus, and FIG. 6 shows an exemplary embodiment of a vertical adjusting unit which is arranged on the patient positioning apparatus.

DETAILED DESCRIPTION

FIG. 1 shows schematically a magnetic resonance apparatus 10. The magnetic resonance apparatus 10 comprises a scanner unit 11 formed by a magnet unit. In addition, the magnetic resonance apparatus 10 has a patient receiving region 12 for receiving a patient 13. In the present exemplary embodiment, the patient receiving region 12 is configured cylindrically and is surrounded cylindrically in a circumferential direction by the scanner unit 11, e.g. the magnet unit. In principle, however, an embodiment of the patient receiving region 12 deviating therefrom is readily conceivable. The patient 13 may be pushed and/or moved by means of a patient positioning apparatus 14 of the magnetic resonance apparatus 10 into the patient receiving region 12. For this purpose, the patient positioning apparatus 14 has a patient table 15, which is configured to be movable within the patient receiving region 12. For instance, the patient table 15 is mounted to be movable in the direction of a longitudinal extent of the patient receiving region 12 and/or in the z-direction.

The scanner unit 11, e.g. the magnet unit, comprises a superconducting main field magnet 16 for generating a strong and constant main magnetic field 17. Furthermore, the scanner unit 11, e.g. the magnet unit, has a gradient coil unit 18 for generating magnetic field gradients that are used for position encoding during an imaging process. The gradient coil unit 18 is controlled by means of a gradient control unit 19 of the magnetic resonance apparatus 10. The scanner unit 11, e.g. the magnet unit, further comprises a radiofrequency antenna unit 20 for exciting a polarization, which forms in the main magnetic field 17 generated by the main field magnet 16. The radiofrequency antenna unit 20 is controlled by a radiofrequency antenna control unit 21 of the magnetic resonance apparatus 10 and radiates radiofrequency magnetic resonance sequences into the patient receiving region 12 of the magnetic resonance apparatus 10.

For controlling the main field magnet 16, the gradient control unit 19 and, for controlling the radiofrequency antenna control unit 21, the magnetic resonance apparatus 10 has a system control unit 22. The system control unit 22 centrally controls the magnetic resonance apparatus, for example, the execution of a pre-determined imaging gradient echo sequence. In addition, the system control unit 22 comprises an evaluation unit (not shown in detail) for evaluating medical image data which is captured during the magnetic resonance examination.

For control of a movement of the patient positioning device 14, e.g. the patient table 15, the patient positioning apparatus 14 has a patient table control unit 26. In the exemplary embodiment under consideration, the patient table control unit 26 is integrated within the system control unit 22 of the magnetic resonance apparatus 10. In principle, the patient table control unit 26 may also be configured separately from the system control unit 22 of the magnetic resonance apparatus 10.

Furthermore, the magnetic resonance apparatus 10 comprises a user interface 23, which is connected to the system control unit 22. Control information such as, for example, imaging parameters and reconstructed magnetic resonance images may be displayed on a display unit 24, for example, on at least one monitor, of the user interface 23 for medical operating personnel. In addition, the user interface 23 has an input unit 25 by means of which information and/or parameters can be input by the operating medical personnel during a scanning procedure.

For an adjustment of a vertical position of the patient table 15, the magnetic resonance apparatus 10 has a vertical adjusting unit 100, 200, 300, 400, wherein the vertical adjusting unit 100, 200, 300, 400 provides at least two different vertical positions for a positioning of the patient table 15 within the patient receiving region 12. In FIG. 1, the vertical adjusting unit 100, 200, 300, 400 is shown purely schematically. For a further embodiment of the vertical adjusting unit 100, 200, 300, 400, reference is made to FIGS. 2 to 6.

The magnetic resonance device 10 shown in FIG. 1 may comprise further components that magnetic resonance apparatuses 10 typically have. A general mode of operation of a magnetic resonance apparatus 10 is also known to a person skilled in the art, so that a detailed description of the further components is not included.

FIGS. 2 and 3 show a first exemplary embodiment of the vertical adjusting unit 100. FIG. 2 shows a portion of a magnetic resonance apparatus 10. This portion comprises a cross-section of the patient receiving region 12. At least one vertical adjusting element 101, 102 of the vertical adjusting unit 100 is arranged within the patient receiving region 12. In the present exemplary embodiment, the vertical adjusting unit 100 has two vertical adjusting elements 101, 102. The two vertical adjusting elements 101, 102 are each formed by passive vertical adjusting elements 101, 102. The two vertical adjusting elements 101, 102 each comprise a side guide 103 which is arranged within the patient receiving region 12. The two side guides 103 are configured for guiding the patient table 15 within the patient receiving region 12. Each of the two side guides 103 is arranged on an edge region 104 of the patient receiving region 12 and extends in the longitudinal direction through the patient receiving region 12. The two side guides 103 are arranged at different, e.g. mutually opposite sides and/or edge regions 104 of the patient receiving region 12. Between the two side guides 103, the patient table 15 of the patient positioning apparatus 14 is guided within the patient receiving region 12.

Each of the two vertical adjusting elements 101, 102, e.g. each of the two side guides 103 may have at least two different receiving regions 105, 106, 107 for receiving the patient table 15. In the present exemplary embodiment, each of the two vertical adjusting elements 101, 102, e.g. each of the two side guides 103, has three receiving regions 105, 106, 107 for receiving the patient table 15. The individual receiving regions 105, 106, 107 are each configured as guide rails. In this way, the vertical adjusting unit 100 has three defined vertical positions for the patient table 15. In the individual receiving regions 105, 106, 107, depending upon the selected vertical adjusting position, sliding elements 109 of the patient table 15, such as sliding rollers, are mounted to be movable in the horizontal direction.

For an introduction of the patient table 15 into one of the three receiving regions 105, 106, 107, the vertical adjusting unit 100 has a further vertical adjusting element 108, which is arranged on the patient positioning apparatus 14, as shown in FIG. 3 illustrating a side view of the magnetic resonance apparatus 10 with the vertical adjusting unit 100. The further vertical adjusting element 108 comprises an active vertical adjusting element 108, wherein by means of the active vertical adjusting element 108, a vertical position of the patient table 15 may be adjusted directly from the three vertical positions available and/or a height of the patient table 15 can be set. The active vertical adjusting element 108 may therein comprise, for example, a scissor lift and/or further active vertical adjusting elements 108 that a person skilled in the art deems useful.

A control of the vertical adjusting unit 100, e.g. of the active vertical adjusting element 108 of the vertical adjusting unit 100 arranged on the patient positioning apparatus 14, takes place by means of the patient table control unit 26 of the patient positioning apparatus 14. For this purpose, the patient table control unit 26 has software which, on execution by a processor of the patient table control unit 26 carries out a control of the vertical adjusting unit 100. By means of the user interface 23 of the magnetic resonance apparatus 10, a user can therein select a vertical position and/or a height for the patient table 15 and the adjustment of the selected vertical position and/or the height of the patient table 15 takes place automatically by means of the patient table control unit 26. Therein, the active vertical adjusting element 108 is controlled accordingly by the patient table control unit 26. If no vertical position and/or height for the patient table 15 is selected by the user, then the patient table 15 is positioned by the patient table control unit 26 in the middle position of the three vertical positions of the patient table 15, wherein this middle vertical position of the patient table 15 comprises a base position of the patient table 15 in the vertical direction.

Following an adjustment of a vertical position of the three vertical positions of the patient table that are available, an introduction of the patient table 15 into the patient receiving region 12 takes place, wherein the patient table 15 is herein introduced dependent upon the adjusted height and/or the adjusted vertical position into one of the three receiving regions 105, 106, 107 of the two passive vertical adjusting elements 101, 102 of the patient receiving region 12. The introduction of the patient table 15 is also controlled by the patient table control unit 26 which, for this purpose, controls a horizontal adjusting unit (not shown in detail) of the patient positioning apparatus 14.

FIG. 4 shows an alternative exemplary embodiment of the vertical adjusting unit to that in FIGS. 2 and 3. In principle, substantially the same components, features, and functions are identified with the same reference signs. The following description describes the differences from the exemplary embodiment in FIGS. 2 and 3, wherein with regard to components, features and functions which remain the same, reference can be made to the description of the exemplary embodiment shown in FIGS. 2 and 3.

In FIG. 4, the magnetic resonance apparatus 10 is shown with the patient table 15 and a vertical adjusting unit 200. The vertical adjusting unit 200 has a vertical adjusting element 201 which is arranged within the patient receiving region 12 of the magnetic resonance apparatus 10. The vertical adjusting element 201 herein comprises a passive vertical adjusting element 201, which is configured for receiving the patient table 15 within the patient receiving region 12. The vertical adjusting element 201 is herein arranged on a rear-side opening 27 of the patient receiving region 12 and protrudes into the patient receiving region 12. For instance, the vertical adjusting element 201 comprises a type of support in order to support the patient table 15 at its end 203 facing in the travel direction 202.

The patient table 15 is herein configured such that an end 203 of the patient table 15 protruding into the patient receiving region 12 is freely floating. The end 203 of the patient table 15 protruding into the patient receiving region 12 therein comprises an end 203 of the patient table 15 facing in the travel direction during a process of introduction of the patient table 15 into the patient receiving region 12. The patient table 15 is therein initially supported only with an end 206 facing away from the patient receiving region 12 on the patient positioning apparatus 14.

For example, the patient table 13 already has its defined vertical position when it is received by a vertical adjusting element 201 within the patient receiving region 12. The vertical adjusting element 201 arranged within the patient receiving region 12 is also configured as height adjustable so that a position in the vertical direction 204 of the vertical adjusting element 201 arranged within the patient receiving region 12 corresponds to a vertical position of the patient table 15. For instance, the adjustment and/or adaptation of a position in the vertical direction 204 of the vertical adjusting element 201 arranged within the patient receiving region 12 takes place automatically by means of the patient table control unit 26. Therein, the position in the vertical direction 204 of the vertical adjusting element 201 within the patient receiving region 12 is adjusted automatically and/or independently by the patient table control unit 26, dependent upon a current and/or adjusted vertical position of the patient table 15.

An adjustment of a vertical position of the patient table 15 takes place by means of a further vertical adjusting element 205 of the vertical adjusting unit 200. The further vertical adjusting element 205 is arranged on the patient positioning apparatus 14. The further vertical adjusting element 205 comprises an active vertical adjusting element 295, wherein by means of the active vertical adjusting element 205, a vertical position and/or a height of the patient table 15 can be adjusted on the patient positioning apparatus 14. The active vertical adjusting element 205 can therein comprise, for example, a scissor lift and/or further vertical adjusting elements 205 that a person skilled in the art deems useful. By means of the user interface 23 of the magnetic resonance apparatus 10, a user can therein select a vertical position and/or a height for the patient table 15 and the adjustment of the selected vertical position and/or the height of the patient table 15 takes place automatically by means of the patient table control unit 26 via an actuation of the active vertical adjusting element 205. For the adjustment of a vertical position of the patient table 15, the vertical adjusting unit 200 has a vertical adjusting region with a minimum vertical position and a maximum vertical position. The adjustment of a vertical position of the patient table 15 by means of the active vertical adjusting element 205 can therein be selected and/or adjusted as desired within the vertical adjusting region e.g., between the minimum vertical adjusting position and the maximum vertical adjusting position. For instance, the user may select any desired position within the vertical adjusting region which is adjusted, driven by the patient table control unit 26 by means of the active vertical adjusting element 205. If no vertical position and/or height for the patient table 15 is selected by the user, then the patient table 15 is positioned by the patient table control unit 26 into a base position and/or a middle vertical position of the patient table 15.

Following an adjustment of a vertical position of the patient table, an introduction of the patient table 15 into the patient receiving region 12 takes place, wherein the end 203 of the patient table 15 facing toward the travel direction is herein brought in a free-floating manner into the patient receiving region 12. To prevent sagging of the patient table 15, the vertical adjusting element 201 arranged within the patient receiving region 12 engages under the patient table 15 to provide support. For example, the vertical adjusting element 201 arranged within the patient receiving region 12 can be configured such that from a center of the patient receiving region 12, the vertical adjusting element 201 already engages under the patient table 15.

The introduction of the patient table 15 is also controlled by the patient table control unit 26 which, for this purpose, controls a horizontal adjusting unit (not shown in detail) of the patient positioning apparatus 14.

FIG. 5 shows an alternative exemplary embodiment of a vertical adjusting unit to that in FIGS. 2 and 4. In principle, components, features and functions that are substantially the same are identified with the same reference signs. The following description describes the differences from the exemplary embodiments in FIGS. 2 to 4, wherein with regard to components, features, and functions which remain the same, reference is made to the description of the exemplary embodiments shown in FIGS. 2 to 4.

In FIG. 5, the magnetic resonance apparatus 10 is shown with the patient table 15 and a vertical adjusting unit 300. The vertical adjusting unit 300 has a vertical adjusting element 301, which is arranged within the patient receiving region 12. The vertical adjusting element 301 comprises an active vertical adjusting element 301, wherein by means of the active vertical adjusting element 301, a vertical position of the patient table 15 and/or a height of the patient table 15 may be adjusted directly. In the present exemplary embodiment, the vertical adjusting unit 300 has two vertical adjusting elements 301, which are each formed by an active vertical adjusting element 301, wherein in the schematic side view in FIG. 5, only one of the two vertical adjusting elements 301 may be seen. Each of the two vertical adjusting elements 301 is arranged on a guide rail 302 for guiding the patient table 15 within the patient receiving region 12. The two guide rails 302 are arranged on mutually opposite edge regions within the patient receiving region 12.

The individual vertical adjusting elements 301 are each configured in the present exemplary embodiment as a scissor lift so that by means of the vertical adjusting elements 301, a vertical position of the guide rail 302 and thus also of the patient table 15 may be adjusted. Herein, for example, the patient table 15 moves into a base position in the patient receiving region 12. Subsequently, an adjustment of a vertical position of the patient table 15 takes place by means of the two vertical adjusting elements 301 in order to adjust a desired examination position of the patient table 15. Herein, by means of the two vertical adjusting elements 301, the guide rails 302 are brought into the desired vertical position and therewith also the patient table 15. Due to the embodiment of the individual vertical adjusting elements 301 as active vertical adjusting elements 301, e.g. as a scissor lift, a vertical adjusting region with a minimum vertical position and a maximum vertical position of the vertical adjusting unit 300 is available for the adjustment of a vertical position of the patient table 15. The adjustment of a vertical position of the patient table 15 by means of the vertical adjusting element 301 can therein be selected and/or adjusted as desired within the vertical adjusting region, e.g., between the minimum vertical adjusting position and the maximum vertical adjusting position. For instance, the user can select any desired position within the vertical adjusting region which is adjusted, controlled by the patient table control unit 26, by means of the vertical adjusting element 301.

By means of the user interface 23 of the magnetic resonance apparatus 10, a user can therein select a vertical position and/or a height for the patient table 15 and the adjustment of the selected vertical position and/or the height of the patient table 15 takes place automatically by means of the patient table control unit 26 via an actuation of the active vertical adjusting elements 301. If no vertical position and/or height for the patient table 15 is selected by the user, then the patient table 15 is positioned by the patient table control unit 26 into a base position and/or a middle vertical position of the patient table 15.

Alternatively, for this purpose, the two vertical adjusting elements 301 may also be formed as passive vertical adjusting elements 301. Herein, by means of the two vertical adjusting elements 301, the position of the two guide rails 302 can be adjusted before an introduction of the patient table 15 into the desired vertical position of the patient table 15 for the receiving of the patient table 15 in this vertical position. Herein, the patient table 15 is already adjusted to the desired vertical position by means of the vertical adjusting unit 300 and the patient table control unit 26, as already described in detail in relation to FIGS. 2 to 4.

FIG. 6 shows an alternative exemplary embodiment of a vertical adjusting unit to that in FIGS. 2 to 5. In principle, components, features and functions that are substantially the same are identified with the same reference signs. The following description is essentially with respect to the differences from the exemplary embodiments in FIGS. 2 to 5, wherein with regard to components, features and functions which remain the same, reference is made to the description of the exemplary embodiments shown in FIGS. 2 to 5.

In FIG. 6, the magnetic resonance apparatus 10 is shown with the patient table 15 and a vertical adjusting unit 400. The vertical adjusting unit 400 has a vertical adjusting element 401 which is arranged on the patient positioning apparatus 14. The vertical adjusting element 401 comprises an active vertical adjusting element 401, wherein by means of the active vertical adjusting element 401, a vertical position of the patient table 15 and/or a height of the patient table 15 can be adjusted directly. The active vertical adjusting element 401 is arranged on an underside 402 of the patient table 15. For instance, the active vertical adjusting element 401 comprises at least one scissor lift which is arranged on the underside 402 of the patient table 15.

The scissor lift may be arranged such that firstly the patient table 15 may be moved in the horizontal direction into an examination position. For this purpose, the patient table 15 is situated in the base position in the vertical direction. Subsequently, by means of the vertical adjusting element 401, e.g., the scissor lift, said patient table is brought and/or moved into a vertical examination position. In addition, it can also be the case that the scissor lift is arranged between a transport unit of the patient table 15 and the patient table 15, so that the patient table 15 can also be moved and/or displaced in the horizontal direction within the patient receiving region 12 in any desired vertical position of the patient table 15.

On the basis of the embodiment of the individual vertical adjusting elements 401 as an active vertical adjusting element 401, e.g. as a scissor lift, a vertical adjusting region is available for the adjustment of a vertical position of the patient table 15, with a minimum vertical position and a maximum vertical position of the vertical adjusting unit 400. The adjustment of a vertical position of the patient table 15 by means of the vertical adjusting element 401 may therein be selected and/or adjusted as desired within the vertical adjusting region, e.g. between the minimum vertical adjusting position and the maximum vertical adjusting position. For instance, the user can select any desired position within the vertical adjusting region which is adjusted, driven by the patient table control unit 26 by means of the vertical adjusting element 401.

A control of the patient table 15, e.g. an adjustment of a vertical position of the patient table 15, takes place by means of the patient table control unit 26 as described in the description relating to FIGS. 2 to 4.

Although the disclosure has been illustrated and described in detail with the preferred exemplary embodiment, the disclosure is not restricted by the examples disclosed and other variations can be derived therefrom by a person skilled in the art without departing from the protective scope of the disclosure.

The various components described herein may be referred to as "units." As described herein, these components may be implemented via any suitable combination of hardware and software components. This may include FPGAs, processors, processing circuitry, or other suitable hardware components configured to execute instructions or computer programs that are stored on a suitable computer readable medium. Regardless of their particular implementation, these components may alternatively be referred to herein as processors or processing circuitry.

What is claimed is:

1. A magnetic resonance apparatus, comprising:
a scanner unit;
a patient receiving region partially surrounded by the scanner unit; and
a patient positioning apparatus having a patient table that is movable within the patient receiving region,
wherein the patient positioning apparatus includes a vertical positioner configured to adjust a vertical position of the patient table within the patient receiving region, the vertical positioner providing different vertical positions for a positioning of the patient table within the patient receiving region,
wherein the vertical positioner comprises a vertical adjusting element that is arranged within the patient receiving region and is coupled to a housing that surrounds the patient receiving region, the vertical adjusting element comprising (i) a first side guide arranged at a first edge of the patient receiving region and comprising a first set of receiving regions configured to receive the patient table, and (ii) a second side guide arranged at a second edge of the patient receiving region and comprising a second set of receiving regions configured to receive the patient table, and
wherein the first edge and the second edge are disposed at opposite sides of the patient receiving region.

2. The magnetic resonance apparatus as claimed in claim 1, wherein the vertical adjusting element is arranged on a rear-side opening of the patient receiving region for receiving the patient table.

3. The magnetic resonance apparatus as claimed in claim 1, wherein the vertical positioner further comprises a powered lift configured to provide a direct adjustment of a vertical position of the patient table within the patient receiving region.

4. The magnetic resonance apparatus as claimed in claim 1, wherein the vertical positioner comprises a further vertical adjusting element that is arranged on the patient positioning apparatus.

5. The magnetic resonance apparatus as claimed in claim 4, wherein the further vertical adjusting element is arranged on an underside of the patient table.

6. The magnetic resonance apparatus as claimed in claim 1, wherein the vertical positioner comprises a further vertical adjusting element comprising a scissor lift.

7. The magnetic resonance apparatus as claimed in claim 1, wherein the vertical positioner provides two different vertical positions for the positioning of the patient table in the patient receiving region within a vertical adjusting region, and
wherein the two vertical positions are adjustable within the vertical adjusting region.

8. The magnetic resonance apparatus as claimed in claim 1, wherein the patient positioning apparatus comprises patient table control circuity configured to control the vertical positioner.

9. The magnetic resonance apparatus as claimed in claim 1, wherein the vertical adjusting element is arranged entirely within the patient receiving region.

10. The magnetic resonance apparatus as claimed in claim 1, wherein an actuating portion of the vertical positioner is arranged entirely within the patient receiving region.

11. The magnetic resonance apparatus as claimed in claim 1, wherein the vertical adjusting element works in conjunction with the vertical positioner, the vertical positioner being positioned outside the patient receiving region.

12. The magnetic resonance apparatus as claimed in claim 11, wherein, after the vertical positioner adjusts the vertical position of the patient table, the vertical adjusting element engages with the patient table under the patient table and within the patient receiving region.

13. The magnetic resonance apparatus as claimed in claim 12, wherein the vertical adjusting element engages with the patient table at a center of the patient receiving region.

14. The magnetic resonance apparatus of claim 3, wherein the powered lift is positioned at an end of the patient receiving region.

15. The magnetic resonance apparatus of claim 3, wherein the powered lift is positioned at a center of the patient receiving region.

16. The magnetic resonance apparatus of claim 1, wherein respective ones of the first set of receiving regions and the second set of receiving regions that are opposite to one another provide different predetermined vertical positions for receiving the patient table to thereby adjust the vertical position of the patient table within the patient receiving region.

17. The magnetic resonance apparatus of claim 1, wherein each of the first side guide and the second side guide extends in a longitudinal direction through and within the patient receiving region.

* * * * *